US00PP31165P3

(12) United States Plant Patent
Stemkens

(10) Patent No.: US PP31,165 P3
(45) Date of Patent: Dec. 3, 2019

(54) *VERBENA* PLANT NAMED 'VEAZ0048'

(50) Latin Name: *Verbena hybrida*
Varietal Denomination: VEAZ0048

(71) Applicant: SYNGENTA PARTICIPATIONS AG, Basel (CH)

(72) Inventor: Henricus Godefridus Wilhelmus Stemkens, Andijk (NL)

(73) Assignee: Syngenta Participations AG, Basel (CH)

( * ) Notice: Subject to any disclaimer, the term of this patent is extended or adjusted under 35 U.S.C. 154(b) by 0 days.

(21) Appl. No.: 16/350,056

(22) Filed: Sep. 20, 2018

(65) Prior Publication Data

US 2019/0104670 P1 Apr. 4, 2019

(51) Int. Cl.
*A01H 5/02* (2018.01)
*A01H 6/86* (2018.01)

(52) U.S. Cl.
USPC ..... Plt./308
CPC ..... *A01H 6/86* (2018.05)

(58) Field of Classification Search
USPC ..... Plt./308
CPC ..... A01H 5/02; A01H 5/00
See application file for complete search history.

*Primary Examiner* — Kent L Bell
(74) *Attorney, Agent, or Firm* — Dale Skalla

(57) ABSTRACT

A new *Verbena* plant named 'VEAZ0048' particularly distinguished by deep purple large sized flowers with a large white eye, large inflorescences, deep green foliage and a semi-trailing plant habit.

1 Drawing Sheet

Latin name of the genus and species of the plant claimed: *Verbena hybrida.*

Varietal denomination: 'VEAZ0048'.

BACKGROUND OF THE NEW PLANT

The present invention comprises a new *Verbena*, botanically known as *Verbena hybrida*, and hereinafter referred to by the variety name 'VEAZ0048'.

'VEAZ0048' is a product of a planned breeding program. The new cultivar has deep purple large sized flowers with a large white eye, large inflorescences, deep green foliage and a semi-trailing plant habit.

'VEAZ0048' originated from a hybridization made in August 2012 in a greenhouse in Enkhuizen, The Netherlands.

The female parent was an unpatented, proprietary plant designated 'R1315-6' with purple flower color and a small white eye and a trailing plant habit. This has smaller flowers and lighter green leaves.

The male parent of 'VEAZ0048' is unknown because it was a mixture of pollen from the plants in the field.

The seed was sown in February 2013 in a greenhouse in Enkhuizen, The Netherlands. 'VEAZ0048' was selected as one flowering plant within the progeny of the stated cross in August 2013.

The first act of asexual reproduction of 'VEAZ0048' was accomplished when vegetative cuttings were propagated from the initial selection in August 2013 in a greenhouse in Enkhuizen, The Netherlands.

BRIEF SUMMARY OF INVENTION

Horticultural examination of plants grown from cuttings of the plant initiated in August 2013, and continuing thereafter, has demonstrated that the combination of characteristics as herein disclosed for 'VEAZ0048' are firmly fixed and are retained through successive generations of asexual reproduction.

'VEAZ0048' has not been observed under all possible environmental conditions. The phenotype may vary significantly with variations in environment such as temperature, light intensity, and day length.

A Plant Breeder's Right for this cultivar was applied for in the European Union on Oct. 2, 2017, No. 2017/2451. 'VEAZ0048' has not been made publicly available prior to the effective filing date of this application, notwithstanding any disclosure that may have been made less than one year prior to the effective filing date of this application by the inventor or another who obtained 'VEAZ0048' directly from the inventor.

The following traits have been repeatedly observed and are determined to be basic characteristics of the new variety. The combination of these characteristics distinguishes this *Verbena* as a new and distinct variety.

BRIEF DESCRIPTION OF THE PHOTOGRAPHS

The accompanying photographic drawings show typical flower and foliage characteristics of 'VEAZ0048' with colors being as true as possible with an illustration of this type.

DETAILED BOTANICAL DESCRIPTION

Figure 1:
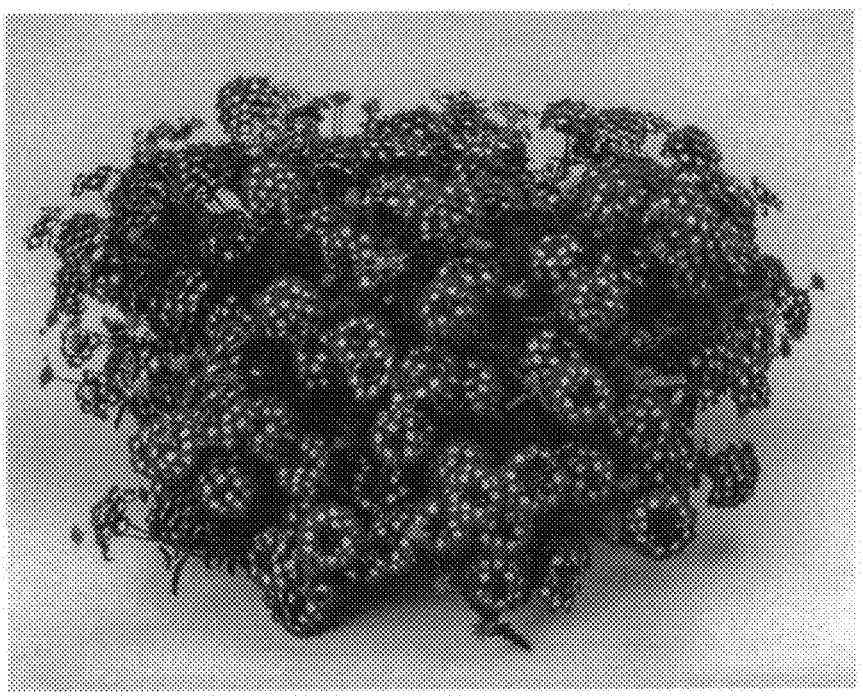
FIG. 1 shows three flowering plants of the new variety in a hanging-basket.
Figure 2:
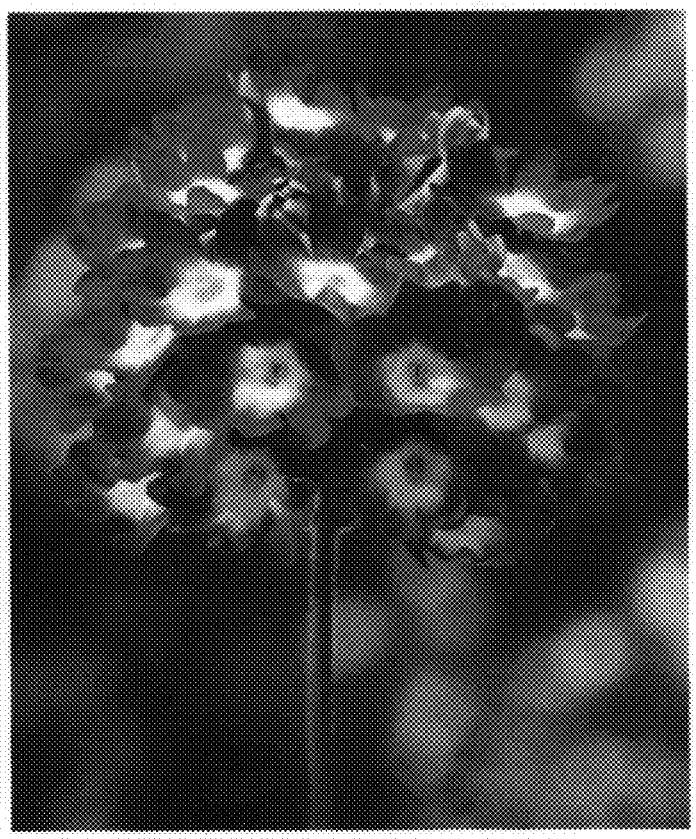
FIG. 2 is a close-up of the inflorescence. The plants were about 12 weeks of age.

The plant descriptions and measurements were taken in Enkhuizen, The Netherlands on Jul. 28, 2018 outdoors in a hanging basket. The plants used were about 12 weeks of age, growing in a 23 cm hanging basket, 3 plants each.

The aforementioned photographs were taken in Gilroy, Calif. USA, as described.

Color references are made to The Royal Horticultural Society Colour Chart (R.H.S.) 2001.

TABLE 1

DIFFERENCES BETWEEN THE NEW VARIETY 'VEAZ0048' AND A MOST SIMILAR VARIETY

| | 'VEAZ0048' | 'Empress Flair Purple Charm' (Not patented) |
|---|---|---|
| Flower color: | Purple with big white eye | Purple with white eye |
| Plant habit: | Semi-trailing | Upright |
| Leaf size: | Large | Medium |

Plant:

*Form, growth and habit.*—Herbaceous, upright vigorous and free branching.

*Plant height.*—14.0 cm.

*Plant height (inflorescence included).*—20.0 cm.

*Plant width.*—38.0 cm.

Roots:

*Number of days to initiate and produce roots.*—10-13 days at about 22 degrees C.

*Type.*—Fine, fibrous, free branching.

*Color.*—RHS N155B but whiter.

Foliage:

*Arrangement.*—Opposite, simple.

*Immature, leaf color, upper surface.*—RHS 138B.

*Immature, leaf color, lower surface.*—RHS 137C.

*Mature, leaf color, upper surface.*—RHS 137A.

*Mature, leaf color, lower surface.*—RHS 137B.

*Length.*—4.5 cm.

*Width.*—2.8 cm.

*Shape.*—Ovate.

*Base shape.*—Cordate.

*Apex shape.*—Acute.

*Margin.*—Entire.

*Texture, upper surface.*—Densely pubescent.

*Lower surface.*—Canescent; glandular hairs.

*Color of veins, upper surface.*—RHS 144B.

*Color of veins, lower surface.*—RHS 147C.

*Pattern of veining.*—Pinnate.

*Petiole, color.*—RHS 147C.

*Petiole, length.*—0.4 cm.

*Petiole, width.*—0.18 cm.

*Texture.*—Hirsute; glandular hairs.

Stem:

*Branching characteristics.*—Potentially at every node.

*Quantity of main branches per plant.*—About 10.

*Color of stem.*—RHS 143B.

*Stem length.*—18-22 cm.

*Stem width.*—0.4 cm.

*Length of internodes.*—2.5 to 3.5 cm.

*Texture.*—Canescent.

*Color of peduncle.*—RHS 144B.

*Length of peduncle.*—4.2 to 6.3 cm.

*Peduncle diameter.*—0.2 cm.

*Texture.*—Canescent.

Inflorescence:

*Type.*—Umbel-like, but actually a spike, umbrella-shaped to nearly semi-spherical.

*Blooming habit.*—Continuously flowering through the summer months.

*Lastingness of individual blooms on the plant.*—About 4 days in the greenhouse.

*Fragrance.*—None.

*Number of inflorescences per plant.*—About 43 at various stages.

*Horizontal diameter of inflorescence.*—About 6.5 cm.

*Depth of inflorescence.*—4.5 cm.

*Number of florets per inflorescence (including any buds at the time).*—21.

Bud (just when opening/showing color):

*Color.*—RHS 79D, purple, with RHS 148C.

*Length.*—0.4 cm.

*Width.*—0.3 cm.

*Shape.*—Tubular with bulbous apex.

Floret:

*Form.*—Sessile; salverform, composed of 5 partly fused petals with a base of a narrow tube.

*Immature color, 2 top petals, upper surface.*—RHS N79B with RHS N87B shades and 1 mm RHS N155C eye towards the center of the flower.

*Immature color, 2 top petals, lower surface.*—RHS 77D fading to lighter.

*Immature color, 3 lower petals, upper surface.*—RHS N79C, with a white, RHS 155D, eye of 2 mm towards the center of the flower.

*Immature color, 3 lower petals, lower surface.*—RHS N80D.

*Mature color, 2 top petals, upper surface.*—RHS N79C with RHS N87C shades, and 1 mm RHS N155B eye towards the center.

*Mature color, 2 top petals, lower surface.*—RHS N82A.

*Mature color, 3 lower petals, upper surface.*—RHS N79D with a white eye, RHS 155D, towards the center.

*Mature color, 3 lower petals, lower surface.*—RHS 84C.

*Floret diameter.*—2.6 cm.

*Floret length (depth).*—2.5 cm.

*Petal length.*—1.6 cm.

*Petal width.*—1 cm.

*Shape.*—Obcordate.

*Apex shape.*—Emarginate.

*Margin.*—Entire.

*Petal texture, upper surface.*—Papillose.

*Petal texture, lower surface.*—Glabrous.

*Corolla tube length.*—1.6 cm.

*Corolla tube width.*—0.15 cm.

*Corolla tube color inside.*—RHS 150D.

*Tube color outside.*—RHS 150D to RHS 145D at floret base.

*Corolla texture, inside.*—Papillose, long white hairs and short hairs.

*Corolla texture, outside.*—Glabrous.

*Throat hair color.*—RHS 155D but whiter.

Calyx:

*Type.*—Five sepals whose margins are fused to each other along their length, with a transparent membrane of less than 0.1 cm in width, and with one smaller sepal attached to the base of the calyx.

*Color of sepals.*—RHS 144B.

*Length of sepals.*—1.2 cm.

*Width of sepals.*—0.2 cm.

*Sepal shape.*—Fused, linear.

*Apex shape.*—Acute.

*Margins.*—Entire.

*Texture.*—Densely covered with short hair, also glandular hairs.

Reproductive organs:

Gynoecium:

*Pistil.*—1.

*Pistil length.*—1.5 cm.

*Style color.*—RHS N144C.

*Style length.*—1.4 cm.

*Stigma color.*—RHS 144A.

*Ovary color.*—RHS 144B.

*Ovary length.*—0.2 cm.

*Ovary width.*—0.1 cm.

Androecium:

*Stamens.*—Anthers and filaments fused to upper half of corolla tube; four anthers with two pollen sacs per anther.

*Color of filaments.*—RHS 151C.

*Filament length.*—0.1 cm.

*Anther color.*—RHS 151C.

*Anther length.*—0.1 cm.

*Pollen amount.*—Little.

*Pollen color.*—RHS 1C.

Fertility/seed set: Neither seed nor fruit production has been observed.

Disease/pest resistance: Resistance to pathogens and pests common to *Verbena* has not been observed.

What is claimed is:

1. A new and distinct variety of *Verbena* plant named 'VEAZ0048' substantially as illustrated and described herein.

* * * * *